United States Patent [19]
Hall

[11] Patent Number: 5,243,996
[45] Date of Patent: Sep. 14, 1993

[54] SMALL-DIAMETER SUPERELASTIC WIRE GUIDE

[75] Inventor: Todd Hall, Bloomington, Ind.

[73] Assignee: Cook, Incorporated, Bloomington, Ind.

[21] Appl. No.: 816,810

[22] Filed: Jan. 3, 1992

[51] Int. Cl.$^5$ .................................................. A61B 5/00
[52] U.S. Cl. .................................... 128/772; 128/657; 604/95; 604/164; 604/280; 604/281
[58] Field of Search ............... 128/657, 658, 772; 604/95, 165, 280, 164, 281, 282; 623/1; 606/192

[56] References Cited

U.S. PATENT DOCUMENTS

| | | | |
|---|---|---|---|
| 3,789,841 | 2/1974 | Antoshkiw | 128/772 |
| 4,538,622 | 9/1985 | Samson et al. | 128/772 |
| 4,545,390 | 10/1985 | Leary | 128/772 |
| 4,619,274 | 10/1986 | Morrison | 128/772 |
| 4,664,113 | 5/1987 | Frisbie et al. | |
| 4,721,117 | 1/1988 | Mar et al. | 128/772 |
| 4,748,986 | 6/1988 | Morrison et al. | 128/772 |
| 4,763,647 | 8/1988 | Gambale | 128/657 |
| 4,832,047 | 5/1989 | Sepetka et al. | 128/657 |
| 4,846,186 | 7/1989 | Box et al. | 128/657 |
| 4,846,193 | 7/1989 | Tremulis et al. | 128/772 |
| 4,925,445 | 5/1990 | Sakamoto et al. | 604/95 |
| 4,971,490 | 11/1990 | Hawkins | 128/772 |
| 4,984,581 | 1/1991 | Stice | 128/772 |
| 4,991,602 | 2/1991 | Amplatz et al. | 604/284 |
| 5,025,799 | 6/1991 | Wilson | 128/772 |
| 5,067,489 | 11/1991 | Lind | 604/164 |
| 5,069,217 | 12/1991 | Fleischhacker, Jr. | 128/657 |
| 5,069,226 | 12/1991 | Yamauchi et al. | 128/772 |
| 5,120,308 | 6/1992 | Hess | 604/95 |
| 5,174,302 | 12/1992 | Palmer | 128/657 |

FOREIGN PATENT DOCUMENTS

| | | | |
|---|---|---|---|
| 90/13329 | 11/1990 | World Int. Prop. O. | 128/772 |
| 91/15152 | 10/1991 | World Int. Prop. O. | 128/772 |

Primary Examiner—Stephen C. Pellegrino
Assistant Examiner—Glenn Dawson
Attorney, Agent, or Firm—Woodard, Emhardt, Naughton, Moriarty & McNett

[57] ABSTRACT

A small diameter wire guide for medical procedures. The wire guide includes a mandrel of metallic superelastic material, such as nitinol, having a diameter less than 0.020 inches and which completes its transformation to austenite at a temperature of about 14° C. The mandrel has a constant diameter over a majority of its length and includes a number of tapered portions and reduced-diameter portions in its distal region. A flexible radiopaque platinum coil is attached at the distal region of the mandrel and coaxially surrounds a portion of the distal region. A smoothly rounded tip is attached to the distal tip of the mandrel and coil and serves to shield the distal end of the coil during the insertion procedure into the patient.

15 Claims, 1 Drawing Sheet

SMALL-DIAMETER SUPERELASTIC WIRE GUIDE

BACKGROUND OF THE INVENTION

This invention relates generally to a wire guide used to position a catheter or other medical tool at a precise location within a patient. In particular, this invention relates to a small-diameter wire guide which can be steered into and along very narrow blood vessels to locate its distal end in a precise position.

In order to negotiate a tortuous path or avoid obstacles during an insertion, wire guides frequently include a floppy tip that is often biased in a certain direction. However, it is desirable that the remaining portion of the wire guide be somewhat elastic and resistant to kinking but still able to transmit a torque so that the physician can reliably change the direction of the bias tip to make a turn or avoid an obstacle while advancing the wire guide into position. It has been found that using a superelastic material (sometimes expressed as "pseudoelastic"), such as a nickel titanium alloy, in the body of the wire guide has significant advantages over conventional steel wire guides, in that nitinol's superelastic properties can allow physicians to reach much more remote locations within the body. In other words, wire guides made of certain nickel titanium alloys simply have improved torque control and more resistance to kinking than conventional stainless steel.

What is needed is an extremely small-diameter wire guide which has improved torque control over conventional stainless steel wire guides, has substantial kink-resistance over the majority of its length, has a distal region of gradual-increasing flexibility and includes an extremely flexible radiopaque distal coil tip.

SUMMARY OF THE INVENTION

A small diameter wire guide according to one embodiment of the present invention comprises a mandrel of metallic superelastic material having a length, an elongated proximal section and a distal region. The superelastic material completes its transformation to austenite at a temperature of about 14° C. The proximal section has a uniform diameter less than 0.020 inches. The distal region of the mandrel has serially disposed a first linear tapered portion, a first reduced diameter portion, a second linear tapered portion and a second reduced-diameter portion. The first tapered portion is adjacent the distal end of the proximal section. A coil having an outer diameter less than 0.020 inches is attached to the distal region and coaxially surrounds the first and second reduced diameter portions as well and the second tapered portion of the distal region. Finally, a smoothly rounded tip is attached to the second reduced diameter portion and shields the distal end of the coil.

In another embodiment of the present invention, there is provided a small diameter wire guide that comprises a mandrel of metallic superelastic material having a length, an elongated proximal section and a distal region. The superelastic material completes its transformation to austenite at a temperature of about 14° C. The proximal section has a uniform diameter less than 0.020 inches. The distal region of the mandrel has serially disposed a first linear tapered portion, a first reduced diameter portion, a second linear tapered portion, a second reduced-diameter portion, a third linear tapered portion and a third reduced diameter portion. The first tapered portion is adjacent the distal end of the proximal section. A coil having an outer diameter less than 0.020 inches is attached to the distal region and coaxially surrounds the second and third reduced diameter portions and the third linear tapered portion. Finally, a smoothly rounded tip is attached to the second reduced diameter portion and shields the distal end of the coil.

One object of the present invention is to provide an improved small-diameter wire guide.

Related objects and advantages of the present invention will be apparent from the following description.

DESCRIPTION OF THE PREFERRED EMBODIMENT

Figure 1:
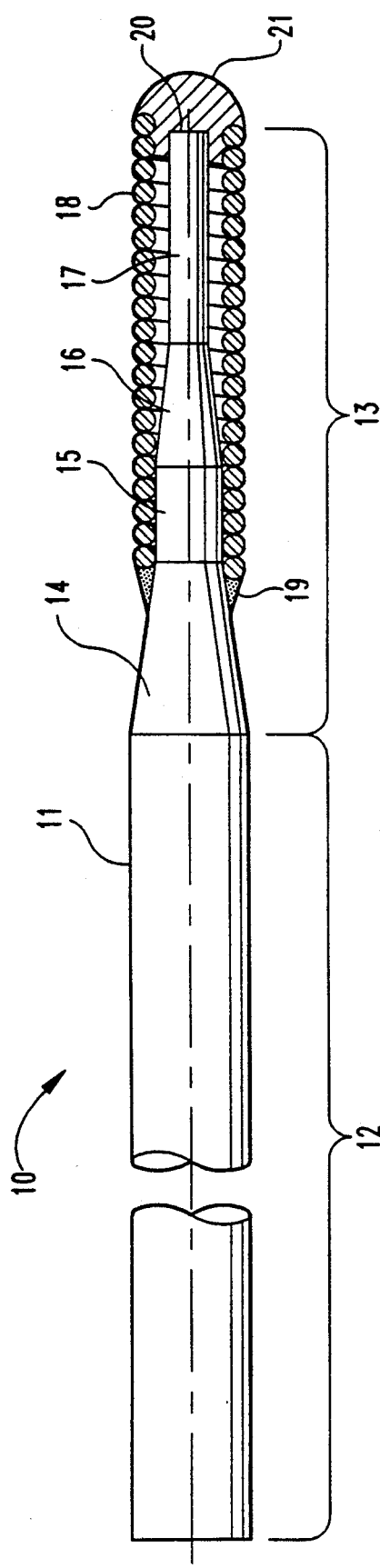
FIG. 1 is a fragmentary longitudinal sectional view of a small-diameter wire guide according to one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, there is shown a wire guide 10 according to one embodiment of the present invention. Wire guide 10 includes a mandrel 11 which is formed from a metallic superelastic material such as nitinol, a nickel titanium alloy. Mandrel 11 is preferably formed from an alloy having 42–50% titanium and 50–58% nickel by weight. Iron and/or chromium, up to 3% by weight, can be added to the nitinol to increase strength. The mandrel material preferably completes its transformation to austenite at a temperature of about 14° C., which is believed to result in greater flexibility than a mandril with a lower transformation temperature without sacrificing torque transmission performance.

Mandrel 11 is divided into elongated proximal section 12 and distal region 13. Elongated proximal section 12 has a uniform diameter less than 0.020 inches, and preferably a diameter of 0.014 or 0.018 inches. The relatively short distal region 13 of mandrel 11 is made up of a first linear tapered portion 14, a first reduced diameter portion 15, a second linear tapered portion 16 and a second reduced diameter portion 17. First tapered portion 14 defines the end of proximal section 12 and the beginning of the distal region 13. Finally, wire guide 10 includes a coil 18 attached to the distal region and coaxially surrounding substantially all but the first tapered portion of the distal region.

Coil 18 is shown attached by weld 19 at a point where the diameter of the first tapered portion 14 equals the inside diameter of the coil. Coil 18, which is preferably formed of a radiopaque platinum-tungsten alloy wire (92% platinum and 8% tungsten) can be bonded to first tapered portion 14 and/or first reduced diameter portion 15 by some conventional means such as gluing, soldering, welding or possibly by a crimping process.

Coil 18 coaxially surrounds most of the distal region of the wire guide and extends a slight distance beyond the distal tip 20 of mandrel 11. Coil 18 could also be made from stainless steel, nitinol or another bio-compatible alloy. A smoothly rounded tip 21 is attached to coil 18 and second reduced diameter portion 17 in order to shield the distal end of the coil during the insertion procedure. Tip 21 can be either a weld or solder. Wire guide 10 can also be coated with at least one polymer layer in order to increase lubricity. One coating could be a hydrophilic and would cover coil 18 and a majority of mandrel 11, leaving the extreme proximal portion of the mandrel uncoated so that the physician can more easily grasp the wire guide.

First linear tapered portion 14 defines a reduction in diameter of at least 40% from that of the elongated proximal section 12. This particular construction allows for greater tip flexibility and easier entry into distal vessels of a patient while still retaining the ability to support a balloon or other catheter. Reduced diameter portion 15 is relatively short, having a length less than 2 cm. The diameter of portion 15 can be made substantially equal to the inner diameter of radiopaque coil 18. Second linear tapered portion 16 defines at least a 25% reduction in diameter from portion 15 to portion 17 at the distal end of mandrel 11.

Wire guides according to this embodiment of the present invention have a length in the range 60–320 cm and preferably have a mandrel length on the order of 185 cm. Only 10 cm of this length is made up of the distal region and the remaining 175 cm is made up of the uniform diameter proximal section 12. Again, proximal section 12 preferably has a diameter of 0.014 or 0.018 inch diameter nitinol wire. First linear tapered portion 14 is preferably approximately 3 cm in length and defines a reduction in diameter down to approximately 0.0065 inches for first reduced-diameter portion 15. Portion 15 is preferably approximately 1.5 cm in length. Second linear taper portion 16 is preferably about 2 cm in length and defines a reduction in diameter down to approximately 0.0035 inch for second reduced-diameter portion 17, which is preferably approximately 3.5 cm in length. Based upon these dimensions, radiopaque coil 18 will preferably be just over 7 cm in length. One variation of this embodiment contemplates a 0.018 inch diameter mandril and a coil having an outer diameter of 0.014 inch. Otherwise, the outer diameter of the coil is generally preferred to be less than or equal to the diameter of proximal section 12.

Figure 2:
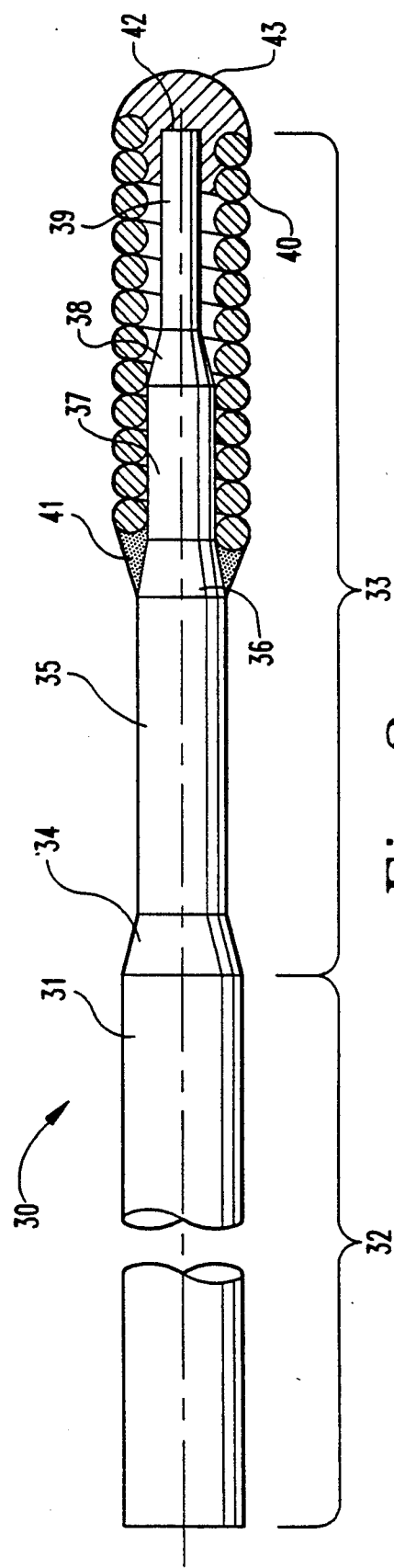
FIG. 2 is a fragmentary longitudinal sectional view of a small-diameter wire guide according to another embodiment of the present invention.

Referring now to FIG. 2, there is shown a wire guide 30 according to another embodiment of the present invention. Wire guide 30, like wire guide 10 discussed earlier, includes a mandrel 31 formed of a metallic superelastic material, such as a nickel titanium alloy which completes its transformation to austenite at a temperature of about 14° C. Mandrel 31 consists of an elongated proximal section 32 and a distal region 33. Distal region 33 is made up of first linear tapered portion 34, first reduced-diameter portion 35, second linear tapered portion 36, second reduced-diameter portion 37, a third linear tapered portion 38 and finally a third reduced-diameter portion 39 at the distal tip of mandrel 31. A coil 40, preferably formed from a radiopaque platinum alloy, is attached with weld 41 to the distal region where the inside diameter of the coil equals that of the mandrel. Coil 40 coaxially surrounds reduced-diameter portion 37, linear tapered portion 38 and reduced-diameter portion 39. A smoothly rounded tip 43 is attached to coil 40 and third reduced diameter portion 39 in order to keep the coil secured to the mandrel and to shield the distal end of the coil during the insertion procedure. This embodiment of the invention is particularly well suited for the performance of PTCA. Wire guide 30 has a soft flexible tip, a stiff proximal shaft, and an area of transition that would be more supportive of a balloon catheter while still being flexible enough to track distal vessels.

The outer diameter of coil 40 is less than or equal to the diameter of elongated proximal section 32. Elongated proximal section 32 is less than 0.020 inches in diameter and preferably is formed from 0.014 or 0.018 inch diameter nitinol wire. Coil 40 is relatively short, normally making up less than 10% of the overall length of mandrel 31. The majority, or over 70% of the length of the distal region, is made up of the first, second and third reduced-diameter portions. In other words, the first second and third linear tapered portions are relatively short in length and define relatively sharp transitions in diameter. The first, second and third tapered portions preferably have lengths that are substantially equal. Like the embodiment described earlier, coil 40 is attached in a conventional manner to the distal region 33.

The mandrel for this embodiment of the present invention can range in length from 60 to 320 cm but preferably has a length on the order of 180 cm. Of this length, only the distal 27 cm make up the distal region portion of mandrel 31. Each of the linear tapered regions are preferably on the order of 2 cm in length and define relatively abrupt changes in the mandril's diameter. First reduced-diameter portion 35 is preferably about 10 cm in length and defines a diameter on the order of 0.010 inches. Second reduced-diameter portion 37 preferably has a length on the order of 5 cm and defines a diameter on the order of 0.0070 inches. Third reduced-diameter portion 39 at the distal tip of the mandrel is preferably about 6 cm in length. Based upon these example dimensions, radiopaque platinum coil 40 would preferably be on the order of 13 cm in length and would extend just beyond the distal tip 42 of reduced-diameter section 39. Coil 40 is generally preferred to have an outer diameter less than or equal to the diameter of proximal section 32. In one specific embodiment, coil 40 has an outer diameter of 0.014 inch and proximal section 32 has a diameter of 0.018 inch.

It is important to note that wire guides having more than three tapered and reduced diameter portions are within the intended scope of this invention. Depending upon the intended application for the wire guide, the distal region could include four or more alternating tapered and reduced diameter portions in the distal region of the mandrel. Furthermore, the lengths of each tapered portion or reduced diameter portion could also be varied from the examples described above without departing from the intended scope of the invention. Finally, the change in diameter of the mandrel defined by each tapered portion could be varied somewhat from the examples described above. It has been found that manufacturing wire guides having a plurality of alternating tapers and reduced diameter portions is much more reliably and easily accomplished than alternatively manufacturing a single elongated taper in the distal region of the mandrel.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A small diameter wire guide comprising:
   a mandrel of metallic superelastic material having a length, an elongated proximal section and a distal region, said superelastic material completing its transformation to austenite at a temperature of about 14° C.;
   said proximal section having a distal end and a uniform diameter less than 0.020 inches;
   said distal region having serially disposed a first linear tapered portion, a first reduced diameter portion, a second linear tapered portion and a second reduced diameter portion, said first tapered portion being adjacent said distal end of said proximal section;
   a coil having a distal end and being attached to said distal region, said coil having an outside diameter less than 0.020 inches, said coil coaxially surrounding said first reduced diameter portion, said second linear tapered portion and said second reduced diameter portion; and
   a smoothly rounded tip attached to said second reduced diameter portion and shielding said distal end of said coil.

2. The wire guide of claim 1 wherein;
   said distal region of said mandrel has a length less than 20 cm.

3. The wire guide of claim 2 further comprising:
   a polymer coating covering said distal region and at least a portion of said proximal section.

4. The wire guide of claim 2 wherein;
   said first linear tapered portion defines at least a 40% decrease in diameter from said proximal section to said first reduced diameter portion.

5. The wire guide of claim 4 wherein;
   said second linear tapered portion defines at least a 25% decrease in diameter from said first reduced diameter portion to said second reduced diameter portion.

6. The wire guide of claim 5 wherein;
   said length of said distal region is about 10 cm.

7. The wire guide of claim 2 wherein;
   said coil is formed from a radiopaque material.

8. The wire guide of claim 7 wherein;
   said outside diameter of said coil is about equal to said uniform diameter of said proximal section.

9. A small diameter wire guide comprising:
   a mandrel of metallic superelastic material having a length, an elongated proximal section and a distal region, said superelastic material completing its transformation to austenite at a temperature of about 14° C.;
   said proximal section having a distal end and a uniform diameter less than 0.020 inches;
   said distal region having serially disposed a first linear tapered portion, a first reduced diameter portion, a second linear tapered portion, a second reduced diameter portion, a third linear tapered portion and a third reduced diameter portion, said first tapered portion being adjacent said distal end of said proximal section;
   a coil having a distal end and being attached to said distal region, said coil having an outside diameter less than 0.020 inches, said coil coaxially surrounding said second reduced diameter portion, said third linear tapered portion and said third reduced diameter portion; and
   a smoothly rounded tip attached to said third reduced diameter portion and shielding said distal end of said coil.

10. The small diameter wire guide of claim 9 wherein;
    said distal region has a length and said first, second and third reduced diameter portions have a combined length which is at least 70% of said length of said distal region.

11. The wire guide of claim 10 wherein;
    said first, second and third tapered portions have lengths that are substantially equal.

12. The wire guide of claim 11 wherein;
    said length of said distal region is about 27 cm.

13. The wire guide of claim 9 further comprising:
    a polymer coating covering said distal region and at least a portion of said proximal section.

14. The wire guide of claim 9 wherein;
    said coil is formed from a radiopaque material.

15. The wire guide of claim 14 wherein;
    said outside diameter of said coil is about equal to said uniform diameter of said proximal section.

* * * * *